United States Patent [19]
Reger et al.

[11] 3,933,851
[45] Jan. 20, 1976

[54] PREPARATION OF AROMATIC 2-IMINO-1,3-DITHIETANES

[75] Inventors: David William Reger; Matthew Michael Nigro, both of Trenton, N.J.

[73] Assignee: American Cyanamid Company, Stamford, Conn.

[22] Filed: Feb. 6, 1974

[21] Appl. No.: 440,112

[52] U.S. Cl............................................ 260/327 M
[51] Int. Cl.²..................................... C07D 339/00
[58] Field of Search..................... 260/327 M, 239.6

[56] References Cited
UNITED STATES PATENTS 3,470,207  9/1969  Addor................................ 260/327
3,484,455  12/1969  Addor................................ 260/327

*Primary Examiner*—Henry R. Jyles
*Assistant Examiner*—C. M. S. Jaisle
*Attorney, Agent, or Firm*—Harry H. Kline

[57] ABSTRACT

There is provided a process for the manufacture of 2-(4-chloro-2-methylphenyl)imino-1,3-dithietane which involves the reaction of a dithiocarbamate salt with a methylene halide in the presence of a base and a sulfide ion in the presence of a ketone solvent to obtain high yields and purity of said 2-(4-chloro-2-methylphenyl)imino-1,3-dithietane.

13 Claims, No Drawings

PREPARATION OF AROMATIC 2-IMINO-1,3-DITHIETANES

The present invention relates to an improved process for the manufacture of 2-(4-chloro-2-methylphenyl)imino-1,3-dithietane in high yield and purity. More particularly, it relates to a process involving the use of a ketonic solvent in the preparation of 2-(4-chloro-2-methylphenyl)imino-1,3-dithietane.

In general, the overall process of the invention can be graphically illustrated by the reaction:

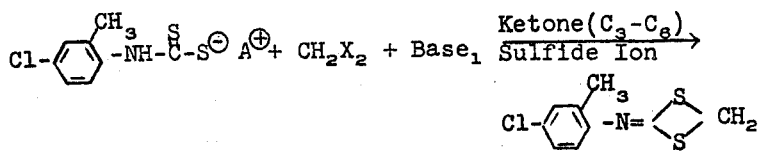

where $A^+$ is a tertiary alkylated ($C_1$-$C_4$) ammonium ion such as trimethyl ammonium; X is a halide, such as bromide or iodide; $Base_1$ is an alkali metal hydroxide, carbonate or bicarbonate, such as sodium hydroxide, potassium hydroxide, sodium carbonate, or sodium bicarbonate, or a tertiary alkylamine, such as trimethylamine or triethylamine. Advantageously the reactant, 4-chloro-2-methylphenyldithiocarbamate salt, can readily be prepared by admixing a base with carbon disulfide and 4-chloro-2-methylaniline according to the overall reaction as follows:

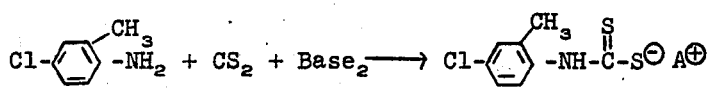

where $Base_2$ may be ammonia or an amine, and $A^+$ is, therefore, an ammonium or tertiary alkyl ($C_1$-$C_4$)-substituted ammonium ion, preferably trimethylammonium. Although it is preferable to employ pure 4-chloro-2-methylaniline as the starting material in this reaction, mixtures of anilines which are obtained by the chlorination of 2-methylaniline can be utilized to prepare pure 4-chloro-2-methyl-phenyldithiocarbamate.

According to the process of this invention, the overall reaction is carried out in a ketonic solvent, such as acetone, methyl ethyl ketone, methyl n-butyl ketone, methyl isobutyl ketone, cyclohexanone or aqueous mixtures thereof, at a temperature ranging between 0° and 35°C. in the presence of a source of sulfide ion derived from ammonium sulfide, sodium sulfide, potassium sulfide, sodium hydrosulfide, or hydrogen sulfide. In practice, the process is preferably carried out in aqueous acetone at temperatures ranging between 10°C. and 30°C. by reacting 1 mole of trialkylammonium-4-chloro-2-methylphenyldithiocarbamate with from 1 to 3 moles of methylene bromide, in the presence of about 1 mole of sodium hydroxide or an equivalent thereof and from about 0.25 to 0.5 mole of aqueous ammonium sulfide ion. The sulfide can be added to the reaction mixture prior to, or subsequent to, the addition of the 4-chloro-2-methylphenyl dithiocarbamate salt. However, to optimize the yield of desired dithietane product, it is preferred to incorporate the ammonium sulfide prior to the addition of the 4-chloro-2-methylphenyldithiocarbamate salt. The addition of the said dithiocarbamate salt to the reaction mixture can be made portionwise over a period of time, but it is preferable to add it as rapidly as possible.

The resultant 2-(4-chloro-2-methylphenyl)imino-1,3-dithietane can be purified by treating the mixture with 1:1.5 equivalents of concentrated hydrochloric acid. The hydrochloride salt is precipitated, then filtered off and washed with an appropriate solvent such as acetone, methyl, ethyl ketone or ethylene chloride. It can then be hydrolyzed by either (a) slurrying with a mixture of water and an organic solvent which is water immiscible, and stirring until all the solids therein have dissolved, followed by separation and evaporation of the organic phase, or (b) slurrying in warm water, and neutralizing with a base such as aqueous ammonia to the end point, and mechanically separating the resulting 2-(4-chloro-2-methylphenyl)imino-1,3-dithietane.

The compound prepared by the process of thisinvention has utility as an ovicidal and larvicidal agent for insects and Acarina. It may also be employed as a chemosterilant for Ixodides. Moreover it has been found to suppress the fecundity in Ixodides.

In practice the compound prepared in accordance with the process of the present invention will generally be used in combination with conventional solid or liquid adjuvants and formulation aids. It may be formulated as a dust, dust concentrates, wettable powders, emulsifiable concentrates or the like and applied to the locus or habitat of the insects and/or Acarina sought to be controlled.

Solid formulations, such as a dust or dust concentrate, can be prepared by grinding the active ingredient together with an inert solid diluent such as attapulgite, kaolin, walnut shell flour, or diatomaceous earth. Where, as in the present invention, the active ingredient is liquid, the formulation may be prepared by spraying said active ingredient on the carrier and thoroughly mixing it with the carrier. The active ingredient may also be dissolved in a solvent such as acetone, lower alcohols, benzene, xylene, toluene, or the like and then sprayed as a dilute solution on the solid carrier. Dusts usually contain from 1% to 15% by weight of active ingredient, whereas concentrates may contain from about 16% to 85% by weight of the active material.

Wettable powders are prepared in the same fashion as dust concentrates, excepting that about 5% to 10% by weight of a surfactant is also added. The wettable powder is then generally dispersed in water or other suitable diluent for application as a dilute liquid dispersion to the plant, animal or locus where insect or Acarina control is desired. Such liquid formulations may also be used as a dip for animals.

The compounds prepared by the process of this invention may also be formulated as an emulsifiable concentrate by dissolving or dispersing about 10% to 75% by weight of the active compound in a suitable solvent or carrier such as a petroleum distillate having a minimum aromatic content of 85% and admixing therewith about 10% by weight of an emulsifier, such polyoxyethylene derivatives and blends with alkyl arylsulfonates. These concentrates may generally, be dispersed in water or other suitable solvent for application as liquid sprays or animal dips.

The invention may be further understood by referring to the examples set forth below which are to be taken merely as illustrative and not by way of limitation. Unless otherwise indicated, all parts and percentages employed herein are by weight.

EXAMPLE 1

Preparation of trimethylammonium 4-chloro-2-methylphenyl dithiocarbamate

To a stirred solution of 56.6 g. (0.40 mole) of 4-chloro-2-methylaniline, 103.2 g. (0.48 mole) of 27.5% aqueous trimethylamine and 28 ml. of acetone at 25°C. is added dropwise 34.4 g. (0.44 mole) of carbon disulfide. The reaction mixture is stirred for 1 hour upon completion of the addition of the carbon disulfide and then filtered. The resulting solid is washed with 75 ml. of ethyl acetate and air dried to obtain 106 g. (95.9% yield) of trimethylammonium 4-chloro-2-methyphenyl dithiocarbamate.

Substituting triethylamine for trimethylamine, in the above procedure, there is obtained triethylammonium 4-chloro-2-methylphenyl dithiocarbamate in similarly good yield.

EXAMPLE 2

Preparation of trimethylammonium 4-chloro-2-methylphenyldithiocarbamate from mixed chlorinated 2-methylanilines To a 250-ml round-bottom flask equipped with a stirrer, thermometer and addition funnel is added at 25°C. 68.2 g. (0.23 mole) of 20.8% aqueous trimethylamine, 28 ml. of acetone, and 28.3 g. of crude chlorinated 2-methylaniline, which by analysis contains 1.5% o-toluidine, 10.4% 6-chloro-2-methylaniline, 75.1% 4-chloro-2-methylaniline, 6.4% 4,6-dichloro-2-methylaniline and 0.7% unknown material. To the reaction mixture is added dropwise 16.7 g. (0.21 mole) of carbon disulfide and the temperature is allowed to rise to a maximum of 35°C. Following the addition of the carbon disulfide, the addition funnel is rinsed with 10 ml. of acetone and the acetone rinsing is added to the reaction mixture.

The reaction mixture is then stirred for 2 hours at ambient temperature and then cooled to 20°C. The precipitate is then separated by filtration and washed with 75 ml. of acetone to obtain 37.10 g. of product which is identified by thin-layer chromatography as 95.5% pure trimethylammonium 4-chloro-2-methylphenyldithiocarbamate. The yield is 89.4%, based on starting 4-chloro-2-methylaniline.

EXAMPLE 3

Preparation of 2-(4-chloro-2-methylphenyl)imino-1,3-dithietane by the portionwise addition of ammonium sulfide to an acetone mixture containing trimethylammonium 4-chloro-2-methylphenyldithiocarbamate To a solution of 4.0 g. (0.1 mole) of sodium hydroxide, 17.45 g. (0.1 mole) of methylene bromide in 28 ml. of acetone cooled to 5°C. is added 32.0 g. (0.1 mole) of triethylammonium 4-chloro-2-methylphenyldithiocarbamate over a period of 15 minutes. After stirring the reaction mixture at 0°-5°C. for 5 minutes the cooling bath is removed and the temperature of the reaction mixture is allowed to rise to reach 25°C.-30°C. After stirring at 25°C.-30°C. for 2.5 hours, the reaction mixture is cooled in an ice bath to 10°C. and 8 g. (0.026 mole) of a 22.5% aqueous solution of ammonium sulfide is added to the reaction mixture. About 20 minutes after the addition of the ammonium sulfide solution is completed, 8.73 g. (0.05 mole) of methylene bromide is added to the reaction mixture.

The addition of ammonium sulfide and methylene bromide to the reaction mixture is repeated, employing 7 ml. of 22.5% aqueous ammonium sulfide and 8.73 g. (0.05 mole) of methylene bromide. The reaction mixture is then stirred until a total of 5 hours has elapsed since the start of the reaction.

The reaction mixture is filtered and the filtrate is concentrated to obtain a crude solid product. The product is extracted four times with 75-ml. portions of benzene and the benzene extract is filtered and concentrated to obtain 27.2 g. of reaction product which is identified by thin-layer chromatography to consist of 73% of the desired product. The yield of the desired product is 86.6%.

EXAMPLE 4

Preparation of 2(4-chloro-2-methylphenyl)imino-1,3-dithietane by one portion addition of ammonium sulfide to a ketone mixture containing trimethylammonium 4-chloro-2-methylphenyldithiocarbamate To a mixture of 100 ml. of methylisobutyl ketone and 8.0 g. of NaOH at 15°C. is added 28 ml. of methylene iodide. While stirring rapidly and with the reaction temperature at 15°C., 55.3 g. (0.2 mole) of trimethylammonium 4-chloro-2-methylphenyldithiocarbamate is added to the reaction mixture over a period of 2 hours while controlling the reaction exotherm with an ice bath. Immediately after the completion of the addition of the trimethylammonium 4-chloro-2-methylphenyldithiocarbamate is completed, 32 g. (0.1 mole) of a 22% aqueous solution of ammonium sulfide is added dropwise to the reaction mixture while maintaining the temperature of the reaction mixture at 15°C. After the exotherm ceases, the reaction mixture is stirred at room temperature for 2 hours.

The lower layer is then separated, and washed with 25 ml. of methyl isobutyl ketone. The combined ketone solutions are then diluted further with 400 ml. of acetone and the acetone solution is treated dropwise with 27 ml. of concentrated hydrochloric acid while stirring rapidly. The resulting slurry is cooled in an ice bath for an additional 15 minutes, then filtered. The resulting solid is air dried and hydrolyzed by stirring with a mixture of 400 ml. of water and 300 ml. of benzene. The benzene layer is separated and dried over anhydrous magnesium sulfate. After removing the magnesium sulfate by filtration, the filtrate is concentrated to obtain 36.4 g. (79.2% yield) of 2-(4-chloro-2-methylphenyl)imino-1,3-dithietane.

EXAMPLE 5

Preparation of 2-(4-chloro-2-methylphenyl)iminodithietane by one portion addition of ammonium sulfide to the reaction mixture immediately before the addition of trimethylammonium 4-chloro-2-methylphenyldithiocarbamate To 50 ml. of acetone, 4.0 g. (0.1 mole) of sodium hydroxide pels and 14 ml. (0.2 mole) of methylene bromide is added 16.0 g. (0.05 mole) of a 21.2% aqueous solution of ammonium sulfide while stirring the reaction mixture rapidly at 20°C. Immediately after the addition of the ammonium sulfide solution is completed, 27.7 g. (0.10 mole) of trimethylammonium 4-chloro-2-methylphenyldithiocarbamate is added to the reaction mixture over a period of 15 minutes. The temperature of the reaction mixture is then held between 20° and 25°C. for a period of 4 hours.

The reaction mixture is then poured into 300 ml. of water and the organic phase is separated. The aqueous phase is washed with 3 × 30 ml. of methylene chloride and all of the organic phases are then combined. After drying the organic phases over anhydrous magnesium sulfate, the solution is filtered and the filtrate is concentrated to obtain 26.1 g. of crude product.

The crude product is dissolved in 250 ml. of acetone and treated with 14.0 ml. of concentrated hydrochloric acid while stirring rapidly. The resulting slurry is filtered and the product is dried to obtain 22.81 g. (85.7% yield) of 2-(4-chloro-2-methylphenyl)imino-1,3-dithietane hydrochloride.

EXAMPLE 6

Preparation of 2-(4-chloro-2-methylphenyl)imino-1,3-dithietane by a process wherein all of the ammonium sulfide is added before the addition of trimethylammonium 4-chloro-2-methylphenyldithiocarbamate and wherein the latter is subsequently added portionwise at 30-minute intervals To a stirred mixture of 8.0 g. (0.2 mole) of sodium hydroxide pels in 300 ml. of acetone at 10°C. is added 32.0 g. (0.1 mole) of 21% aqueous ammonium sulfide solution and 28 ml. (0.4 mole) of methylene bromide. The temperature is allowed to reach 15°C. and then an amount of 55.3 g. (0.2 mole) of trimethylammonium 4-chloro-2-methylphenyldithiocarbamate is added in portions of 16.3 g., 13 g., and 13 g. at one-half hour intervals. After the addition of the dithiocarbamate salt is completed, the reaction is stirred at room temperature for 2 hours.

The two-phase reaction mixture is split and the aqueous phase is washed with 20 ml. of acetone. The acetone solutions are then combined and placed in the reaction vessel, diluted with 400 ml. of additional acetone and treated with 27 ml. (0.32 mole) of concentrated hydrochloric acid to precipitate a white solid. The resulting slurry is stirred for 15 minutes at 15°C. and filtered to yield 52.25g. of crude 2-(4-chloro-2-methyl)imino-1,3-dithietane hydrochloride.

The hydrochloride salt is stirred in a mixture of 400 ml. of water, 400 ml. of benzene and 10 ml. of concentrated ammonium hydroxide for 45 minutes. The resulting solution is filtered and the organic layer is separated. After drying and removing the solvent, there is obtained 36.44 g. (95% real; 75.3% yield) of 2-(4-chloro-2-methylphenyl)imino-1,3-dithietane.

EXAMPLE 7

Preparation of 2-(4-chloro-2-methylphenyl)imino-1,3-dithietane by a process wherein sodium sulfide solution is added portionwise after the addition of triethylammonium 4-chloro-2-methylphenyldithiocarbamate A mixture of 7 ml. (0.10 mole) of methylene bromide, 10.1 g. (0.10 mole) of triethylamine and 28 ml. of acetone is cooled to 5°C. and 32.0 g. (0.1 mole) of triethylammonium 4-chloro-2-methylphenyldithiocarbamate is added over a period of 15 minutes. The temperature of the solution is allowed to rise to 20°–25°C. and the solution is stirred for 1.5 hours and then cooled to 15°C. and 9.0 g. of sodium sulfide is added. Stirring is continued for one-half hour at 15°C., whereupon 7 ml. (0.10 mole) of methylene bromide is added to the reaction mixture. After stirring for one hour, there are added 9 g. of sodium sulfate and 7 ml. of methylene bromide to the reaction mixture. The solution is stirred until the total reaction time of initiation is 5.5 hours. Work-up of the of organic phase of the reaction mixture gives 23.3 g. of crude product which is converted to 20.5 g. (77.4% yield) of 2-(4-chloro-2-methylphenyl)-imino-1,3-dithietane hydrochloride by treatment with hydrochloric acid.

EXAMPLE 8

Preparation of 2-(4-chloro-2-methylphenyl)imino-1,3-dithietane by a process wherein trimethylammonium 4-chloro-2-methylphenyldithiocarbamate is added portionwise to a reaction mixture containing ammonium sulfide To a rapidly stirred mixture of 10.2 g. (0.25 mole) of sodium hydroxide in 50 ml. of acetone at 10°C. is added sequentially 14.2 g. (0.05 mole) of a 24% aqueous solution of ammonium sulfide and 14 ml. (0.20 mole) of methylene bromide. Immediately thereafter 27.7 g. (0.10 mole) of trimethylammonium 4-chloro-2-methylphenyldithiocarbamate is added to the reaction mixture portionwise over a 15-minute period. The reaction temperature is maintained at 15°C. throughout the period of the addition of the salt. After the addition is completed, the temperature is allowed to rise to 25°C.–30°C. and the mixture is stirred for 2.5 hours.

An amount of 50 ml. of water and 100 ml. of cyclohexane is added to the reaction mixture and the temperature is then increased to 50°C. while the mixture is rapidly stirred for 1 hour. The reaction mixture is cooled and filtered and the organic phase is separated and washed with 2 × 100-ml. portions of dilute aqeuous hydrochloric acid solution (0.4N). The organic phase is then washed with 2 × 100-ml. portions of water and dried over anhydrous magnesium sulfate. After filtering to separate the drying agent and concentrating the filtrate, there is obtained 19.22 g. of a crude oil (93.4% real; 78.2% overall yield) of 2-(4-chloro-2-methylphenyl)imino-1,3-dithietane.

EXAMPLE 9

Preparation of 2-(4-chloro-2-methylphenyl)imino-1,3-dithietane by a process wherein the ammonium sulfide solution is added to the reaction mixture after the addition of trimethylammonium 4-chloro-2-methylphenyldithiocarbamate To a mixture of 100 ml. of acetone, 8.0 g. (0.20 mole) of sodium hydroxide pels, and 28 ml. (0.40 mole) of methylene bromide at 10°C. is added 26.5 g. of trimethylammonium-4-chloro-2-methylphenyldithiocarbamate. The salt is added over a 1-hour period while the temperature is maintained between 15°C.–20°C. After completion of the addition of the salt, 32 g. of 24% aqueous solution of ammonium sulfide (7.7 g. real; 0.11 mole) is added to the reaction mixture over a 10-minute period at 15°C. The resulting reaction mixture is then stirred for 4 hours at 25°C.

The reaction mixture is then poured into a separatory funnel and the lower aqeuous layer is separated. The aqueous layer is washed twice with 100 mls. of acetone and the acetone washings are combined with the organic phase.

The combined acetone solutions are diluted to 500 ml. with additional acetone and the temperature is increased to 55°C. While the temperature is maintained at 55°C., 28 ml. (0.33 mole) of concentrated hydrochloric acid is added dropwise to the reaction mixture to precipitate a white solid. The resulting slurry is stirred at 55°C. for 20 minutes and filtered to obtain 64 g. of crude 2-(4-chloro-2-methylphenyl)imino-1,3-dithietane hydrochloride.

The hydrochloride salt is added to a 3-neck flask equipped with a condenser and stirrer, and containing 92 ml. of toluene and 230 ml. of water. While stirring the contents rapidly, the temperature of the mixture is increased to reflux and held at reflux for 30 minutes. The resulting solution is cooled to 25°C. and separated. The aqueous layer is then separated from the organic layer and back-extracted with toluene. The toluene extracts are combined with the organic phase and concentrated to obtain 37.6 g. (97% real; 79.4% yield) of 2-(4-chloro-2-methylphenyl)imino-1,3-dithietane.

I claim:

1. A method for preparing a compound of the formula:

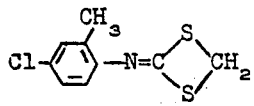

which comprises the steps of: reacting at a temperature ranging from 0°C. to 35°C. 1 mole of (a) a compound of the formula:

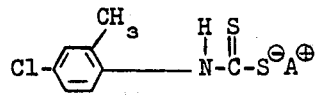

wherein $A^+$ represents a member selected from the group consisting of a tertiary alkyl ($C_1$–$C_4$)-substituted ammonium ion and (b) with from 1.0 to 3.0 molar equivalents of a methylene halide, in the presence of an inorganic or organic base and a sulfide ion having the formula: $Ha'SM_{(2-a\,1\,)}$, wherein a' represents an integer selected from the group consisting of 0, 1 and 2; M represents a member selected from the group consisting of alkali metal, ammonium and primary, secondary, and a tertiary alkyl ($C_1$–$C_4$)-substituted quaternary ammonium ion; in a ($C_3$–$C_6$) ketonic solvent selected from the group consisting of acetone, methyl ethyl ketone, methyl propyl ketone, methyl isopropyl ketone, methyl n-butyl ketone, methyl isobutyl ketone, cyclohexanone and mixtures of water and said ($C_3$–$C_6$) ketonic solvent, and recovering the desired product.

2. A method according to claim 1 wherein the methylene halide is selected from the group consisting of methylene bromide and methylene iodide.

3. A method according to claim 1 wherein the said sulfide ion is selected from the group consisting of ammonium sulfide, sodium sulfide, potassium sulfide, sodium hydrosulfide, potassium hydrosulfide and hydrogen sulfide.

4. A method according to claim 1 wherein the base is selected from the group consisting of an alkali metal hydroxide, an alkali metal carbonate, an alkali metal bicarbonate, ammonia and an alkyl ($C_1$–$C_4$) amine.

5. A method according to claim 1 wherein the reaction is carried out at a temperature between 10°C. and 30°C.

6. A method according to claim 1 wherein the number of equivalents of base relative to sulfide ion is from 1 to 2 times the equivalents of hydrogen (a') in the sulfide source.

7. A method according to claim 2 wherein $A^+$ is trimethylammonium.

8. A method according to claim 3 wherein the methylene halide is methylene bromide and from 1.0 to 3.0 moles of methylene bromide per mole of compound of the formula:

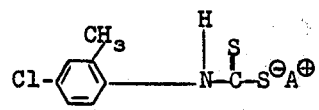

is employed.

9. A method according to claim 4 wherein the sulfide is ammonium sulfide.

10. A method according to claim 1 wherein the base is sodium hydroxide.

11. A method according to claim 1 wherein the solvent is acetone.

12. A method according to claim 1 wherein the solvent is methyl ethyl ketone.

13. A method according to claim 1 wherein the solvent is methyl isobutyl ketone.

* * * * *